United States Patent
Baker (12)

(10) Patent No.: US 6,637,059 B1
(45) Date of Patent: Oct. 28, 2003

(54) INFLATABLE PILLOW FOR USE WITH A HALO RESTRAINT

(76) Inventor: David D. Baker, 9313 Barcroft Dr., Indianapolis, IN (US) 46240

( * ) Notice: Subject to any disclaimer, the term of this patent is extended or adjusted under 35 U.S.C. 154(b) by 0 days.

(21) Appl. No.: 10/219,015

(22) Filed: Aug. 14, 2002

(51) Int. Cl.[7] .................................................. A61F 5/00
(52) U.S. Cl. ........................ 5/644; 5/637; 5/640; 5/643
(58) Field of Search ................................. 297/393, 397; 5/636, 637, 640, 644, 645, 625, 626, 628, 622

(56) References Cited

U.S. PATENT DOCUMENTS

| | | | | | |
|---|---|---|---|---|---|
| 1,510,187 | A | * | 9/1924 | Martin | 297/393 |
| 4,074,373 | A | * | 2/1978 | Garofalo | 5/640 |
| 4,285,081 | A | * | 8/1981 | Price | 5/637 |
| 4,913,135 | A | * | 4/1990 | Mattingly | 602/18 |
| 5,090,073 | A | * | 2/1992 | Nordan et al. | 5/640 |
| 5,274,865 | A | * | 1/1994 | Takehashi | 5/644 |
| 5,544,378 | A | * | 8/1996 | Chow | 5/644 |
| 5,832,550 | A | * | 11/1998 | Hauger et al. | 5/621 |

* cited by examiner

*Primary Examiner*—Michael F. Trettel
(74) *Attorney, Agent, or Firm*—Woodard, Emhardt, Moriarty, McNett & Henry LLP

(57) ABSTRACT

An inflatable pillow for use with a halo-type head immobilization brace having a generally circular head-encircling member secured to a patient's head and a plurality of post members extending from the head-encircling member. The inflatable pillow includes a flexible, generally rectangular base portion, a generally oval inflatable bladder portion connected to the base portion, and means for removably securing the base portion to the post members. The bladder portion is inflatable to expand to fit snugly between the patient's head and the head-encircling member.

13 Claims, 2 Drawing Sheets

INFLATABLE PILLOW FOR USE WITH A HALO RESTRAINT

BACKGROUND OF THE INVENTION

Orthotic (halo) braces are worn by patients recovering from spinal surgery to hold them immobile while healing. A halo brace allows for the most rigid fixation of the cervical spine and is used primarily for multiple level complex cervical spine surgery patients or for patients having unstable fractures. The halo consists of a titanium ring around the patient's head which is held in place by three or more screws anchored in the patient's skull. The ring is attached by three or more bars to a vest worn on the trunk to anchor the device and hold the neck in place. The halo device is worn at all times until the spine heals. The halo immobilizes the head and neck to provide stability for the healing spine. Typically, a patient wearing a halo wears it constantly for between three and nine months while the spinal injury/surgery completely heals.

Although the halo brace is a necessary part of the treatment for recuperating from a serious spinal injury, the halo brace and vest assembly is heavy, bulky, and extremely uncomfortable for the wearer. Since the halo brace assembly cannot be removed from the patient for the duration of the recuperative process, the patient generally finds relaxation and sleep extremely difficult.

There have been attempts to address this problem, one such attempt being described in U.S. Pat. No. 5,210,894 to Minton. The '894 patent describes a pillow for use by the user of a head immobilizing device having a circular member and a plurality of longitudinally extending struts, the pillow having a T-shaped slot which will accommodate the device while allowing the unslotted portion to support the user's head. The '894 pillow, while useful, only supports the uppermost portion of the patient's head and does not provide adjustable support. There therefore remains a need for a device to provide comfort and support to the patient's head interior to the halo. The present invention addresses this need.

SUMMARY OF THE INVENTION

The present invention relates to an inflatable pillow for positioning between a patient's head and a head immobilization halo brace. The halo is typically screwed to the patient's head and has at least two post members extending from the head-encircling band member. The pillow includes an elongated flexible base member, a first post connector coupled to one end of the base member and a second post connector coupled to the other end. An elongated inflatable bladder having at least two independently inflatable chambers is connected to the base member. A check valve is operationally connected to each respective independently inflatable chamber such that the pressure of each chamber may be independently regulated for maximum patient comfort.

One object of the present invention is to provide an improved pillow for use with a halo brace. Related objects and advantages of the present invention will be apparent from the following description.

DETAILED DESCRIPTION OF THE PREFERRED EMBODIMENTS

Figure 1:
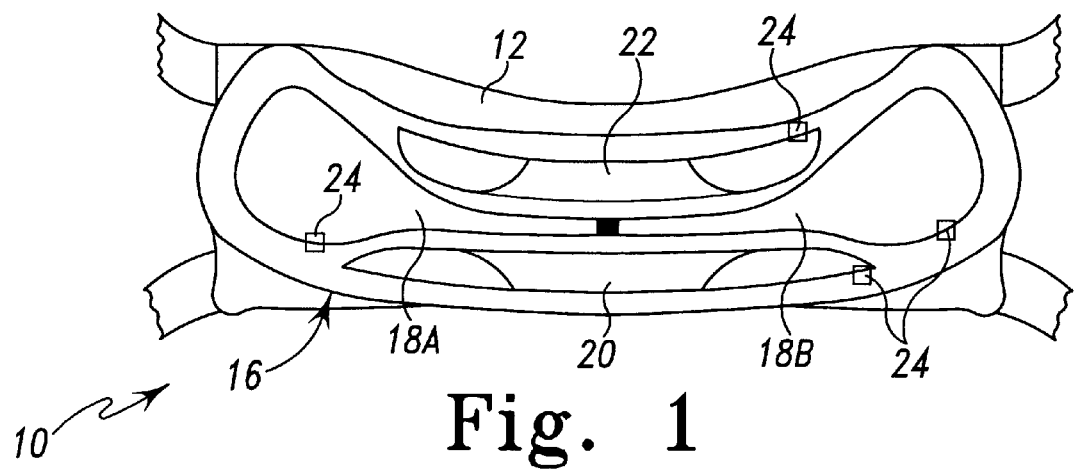
FIG. 1 is a top plan view of a first embodiment of an inflatable pillow of the present invention.
Figure 2:
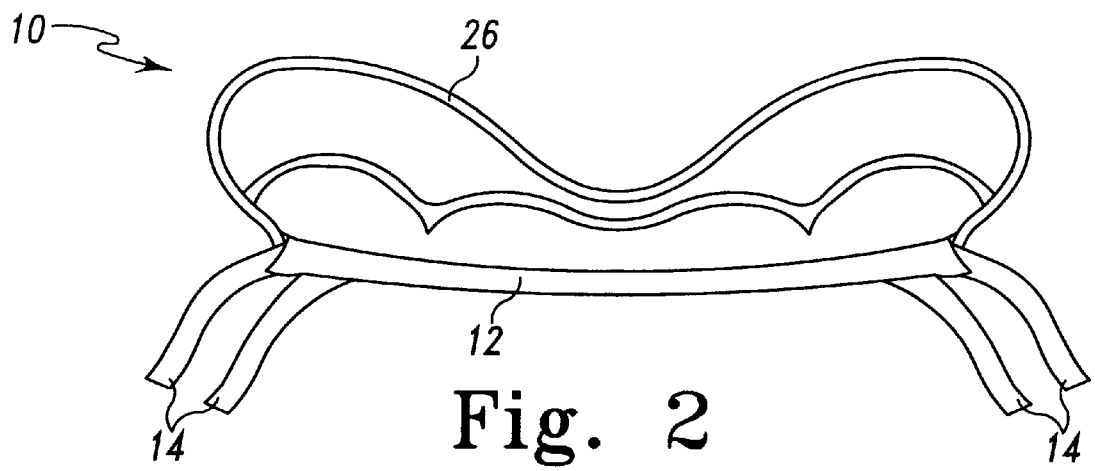
FIG. 2 is a side elevational view of the embodiment of FIG. 1.
Figure 3:
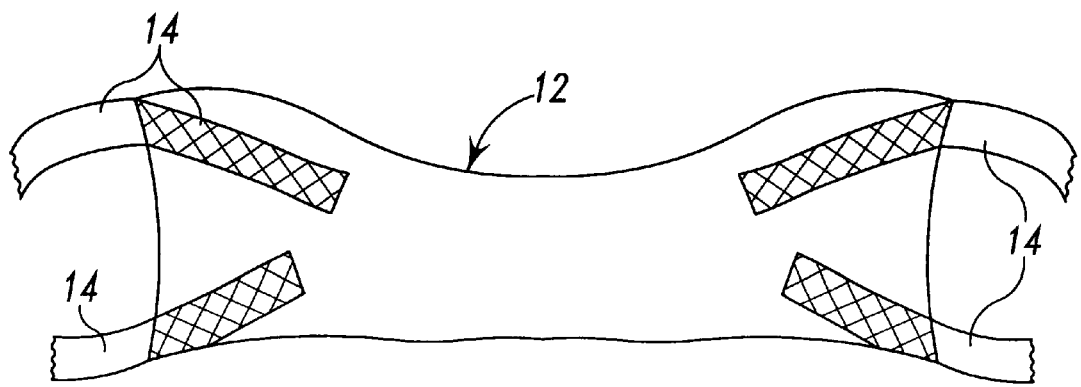
FIG. 3 is a bottom plan view of the embodiment of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIGS. 1–4 illustrate a first embodiment of the present invention, an inflatable pillow 10 for use with a halo-type head brace 11 or head immobilization system. The inflatable pillow 10 includes a generally rectangular or rounded flexible base 12. At either end of the flexible base, releasable connectors 14 are attached to the flexible base 12 and extend therefrom. The releasable connectors are adapted to engage the posts 13 of a halo type brace 11 and firmly affix the base 12 thereto. Preferably, the releasable connectors 14 are of the hook and loop type, such that each connector may include one strip of hook covered material and another mateable strip of loop covered material that can interlockingly engage one another to secure base 12 to a post 15; however, it will be recognized by those skilled in the art that any releasable connector design may be used.

A bladder assembly 16 is connected to the flexible base 12. Preferably, the bladder assembly 16 is generally kidney-shaped and generally extends across the major surface of the flexible base 12. More preferably, the bladder assembly 16 includes a plurality of independently inflatable chambers 17. Still more preferably, the bladder assembly 16 includes a pair of central inflatable chambers 18a and 18b extending generally from the center point of the flexible base 12 towards the respective ends of base 12. In other words, the inflatable chambers 18a and 18b extend generally parallel to the longitudinal axis of the elongated flexible base 12. Also preferably, a bottom elongated inflatable chamber 20 and a top elongated inflatable chamber 22 are positioned opposite one another on either side of the central inflatable chambers 18a and 18b.

The bladder assembly 16 and the flexible base 12 are both preferably formed from a heat sealable plastic material (such as polymer), such that the inflatable chambers can be defined by heat seal lines joining the bladder assembly 16 to the flexible base 12, as is known in the art. Each independently inflatable chamber 17 may be inflated through a respective check valve 24 operationally connected thereto, such that air under pressure may easily enter the bladder assembly 16 through the check valve 24, but the check valve 24 is held shut by a greater pressure inside the bladder assembly 16 than its environment. Such check valves 24 are commonly known in the art and are preferably formed from a polymer or plastic material. The check valves 24 may be attached to the bladder assembly 16 by heat sealing, adhesive, or the like. Bladder assembly 16 is also preferably covered with a fabric cover 26 to provide maximum comfort to the patient using the inflatable pillow 10.

Figure 4:
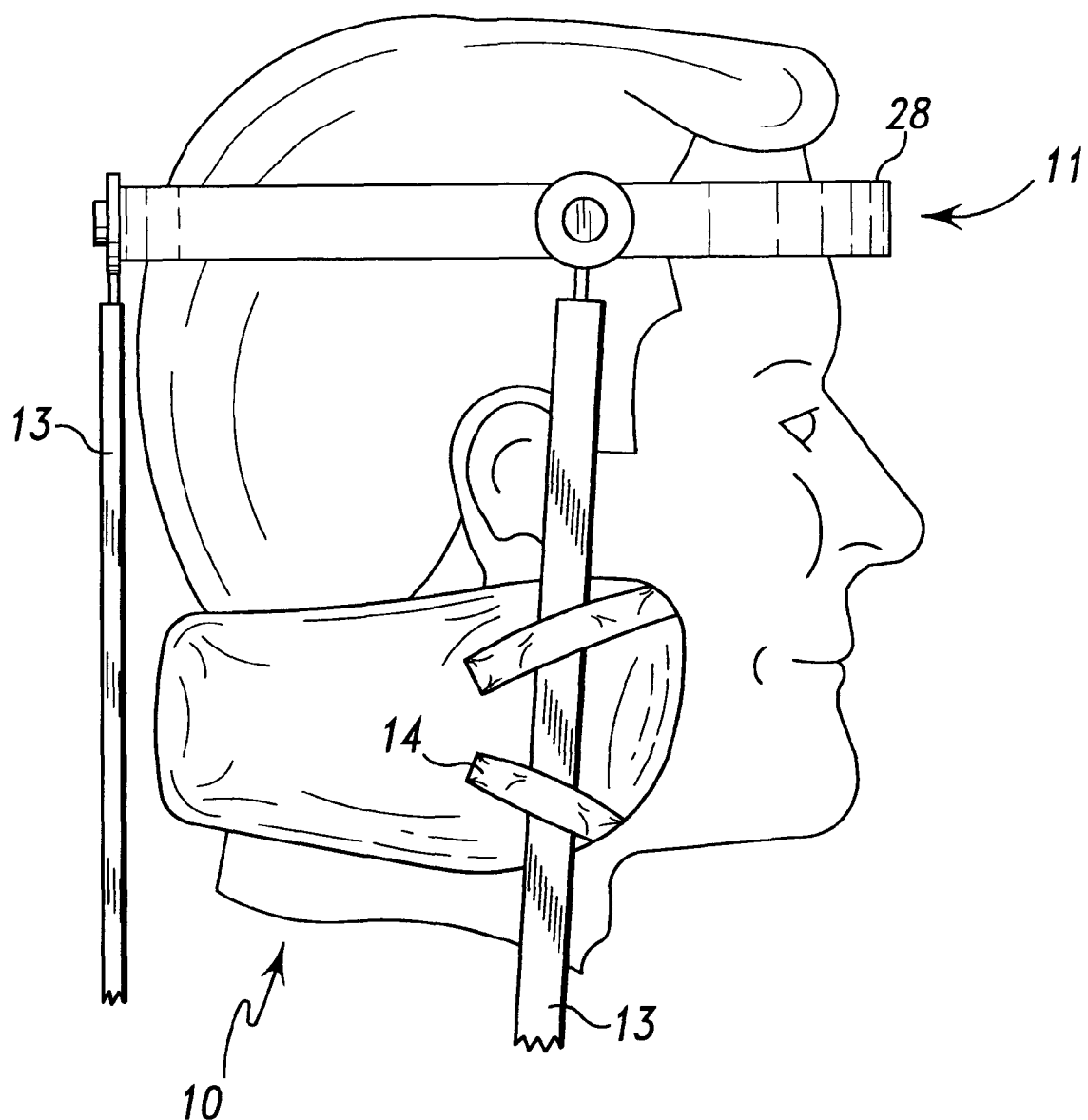
FIG. 4 is a side perspective view of the embodiment of FIG. 1 positioned between a halo brace and a patient's head.

FIG. 4 illustrates in detail the inflatable pillow 10 as positioned adjacent a halo brace and a patient's head. In operation, the inflatable pillow 10 is inserted between the posts 13 of a halo brace 11 and the patient's head in the region of the cheeks and upper neck. Once in position, the releasable connectors 14 may be wrapped around the posts 13 extending from the band portion 28 and secured to themselves in order to hold pillow 10 securely in place. The inflatable compartments 17 are then sequentially inflated, such as by a hand pump, lung power focused through a hose connected between the check valves 24 and an inflator's mouth, or any other convenient pressurization means. Each compartment 17 is inflated sufficiently to maximize the patient's comfort.

The flexible base 12 is preferably a generally rectangular elongated piece of flexible material, such as plastic or rubber, and is more preferably concavely curved along one of its lengthwise sides or otherwise shaped to properly conform to the patient's head.

In order to promote proper healing of some fractures, the halo brace 11 is sometimes installed with the patient's head cocked slightly to one side with respect to the halo brace 11. In this situation, there are different gap widths on either side of the patient's head between the head and the posts 13. Because the pillow 10 of the present invention includes independently inflatable chambers 18–22, these varying gaps can be conveniently filled by the pillow 10 by applying varying amounts of pressurization to the individual inflatable chambers.

It will be apreciated by those having ordinary skill in the art that the pillow 10 provides greatly enhanced comfort to the patient wearing the halo brace 11 by filling in the gaps between the patient's face and neck and the posts 13 of the halo brace 11 during rest or sleep. This not only provides physical support to these areas, but also alleviates the psychological discomfort of laying down and having these areas suspended in midair, which is not perceived by the brain as being an appropriate position for resting.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An inflatable pillow for use with a head immobilization brace having a head-encircling member secured to a patient's head and a plurality of post members extending from the head-encircling member, comprising:
    a flexible, generally rectangular base portion;
    a generally kidney-shaped inflatable bladder portion connected to the base portion; and
    means for removably securing the base portion to the post members;
    wherein the bladder portion is inflatable to expand to fit snugly between the patient's head and the post members.

2. The inflatable pillow of claim 1 wherein the means for removably securing the base portion to the post members includes at least two pair of hook and loop connector strips extending from the base portion.

3. The inflatable pillow of claim 1 further comprising at least one check valve operationally connected to the bladder portion for inflating the bladder portion.

4. The inflatable pillow of claim 1 wherein the bladder portion includes a plurality of independently inflatable chambers and further comprising a plurality of check valves, wherein a check valve is operationally connected to each respective inflatable chamber.

5. The inflatable pillow of claim 1 wherein the base portion and the bladder portion are formed from a polymer material.

6. The inflatable pillow of claim 1 further comprising a halo brace positioned to hold the pillow against the patient's head.

7. An inflatable pillow for positioning between a patient's head and a head immobilization halo having a substantially head-encircling band member connected to the patient's head and at least two post members extending from the band member, comprising:
    an elongated flexible base member having a first end and a second end;
    a first post connector coupled to the first end and a second post connector coupled to the second end;
    an elongated inflatable bladder having at least two independently inflatable chambers and connected to the base member; and
    a check valve operationally connected to each respective independently inflatable chamber.

8. The inflatable pillow of claim 7 wherein the elongated inflatable bladder further comprises:
    a first and a second oppositely positioned inflatable chamber, each respective chamber extending substantially from the center of the base member towards a respective end; and
    a third and fourth oppositely positioned substantially elongate inflatable chamber, each respective chamber positioned extending parallel to and on respective opposite sides of the first and second inflatable chambers.

9. The inflatable pillow of claim 7 further comprising a portable pump adapted to inflate the bladder.

10. The inflatable pillow of claim 8 wherein the inflatable chambers are inflated to different pressures.

11. A method for comforting the head of a patient wearing a halo brace having a substantially head-encircling portion connected to the patient's skull and a plurality of post members extending therefrom, through the use of an inflatable pillow having a plurality of inflatable compartments formed therein, comprising the steps of:
    a) inserting the inflatable pillow between at least some of the plurality of posts and the head; and
    b) sequentially inflating the inflatable compartments;
    wherein each compartment is inflated sufficiently to maximize the patient's comfort.

12. The method of claim 11 wherein the inflatable pillow further comprises:
    an elongated flexible base having a first end and a second end;
    a first releasable connector extending from the first end and a second releasable connector extending from the second end;
    an elongated inflatable bladder connected to the base; and
    a check valve operationally connected to each the bladder.

13. The method of claim 12 wherein the elongated inflatable bladder further comprises a plurality of independently inflatable chambers.

* * * * *